US00PP23816P2

(12) United States Plant Patent
Hartman

(10) Patent No.: US PP23,816 P2
(45) Date of Patent: Aug. 6, 2013

(54) ***CALADIUM* PLANT NAMED 'SWEET CAROLINA'**

(50) Latin Name: *Caladium×hortulanum*
Varietal Denomination: Sweet Carolina

(76) Inventor: Robert Dale Hartman, Lake Placid, FL (US)

( * ) Notice: Subject to any disclaimer, the term of this patent is extended or adjusted under 35 U.S.C. 154(b) by 5 days.

(21) Appl. No.: 13/374,458

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Sweet Carolina', characterized by its upright plant habit; tall plant size; uniform plant habit; vigorous and dense growth habit; fancy-type leaves with greyed purple-colored venation, random red purple-colored spots and mottled light and dark green-colored interveinal areas; and good landscape performance.

5 Drawing Sheets

Botanical designation: *Caladium×hortulanum.*
Cultivar denomination: 'SWEET CAROLINA'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Sweet Carolina'.

The objective of the Inventor's breeding program is to create new *Caladium* plants that have uniform plant habit, exceptional container and garden performance and attractive foliage coloration.

The new *Caladium* plant originated from a cross-pollination made by the Inventor in June, 2002 in Lake Placid, Fla. of *Caladium×hortulanum* 'Grey Ghost', not patented, as the female, or seed, parent with *Caladium×hortulanum* 'Miss Muffet', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sweet Carolina'. These characteristics in combination distinguish 'Sweet Carolina' as a new and distinct *Caladium* plant:

1. Upright plant habit; tall plant size.
2. Uniform plant habit.
3. Vigorous and dense growth habit.
4. Fancy-type leaves with greyed purple-colored venation, random red purple-colored spots and mottled light and dark green-colored interveinal areas.
5. Good landscape performance and tolerant to full sun conditions.

Plants of the new *Caladium* differ primarily from plants of the female parent, 'Grey Ghost', in the following characteristics:

1. Plants of the new *Caladium* are taller than plants of 'Grey Ghost'.
2. Plants of the new *Caladium* and 'Grey Ghost' differ in leaf coloration as leaves of plants of 'Grey Ghost' have white to grey white-colored venation and interveinal areas with green-colored borders.

Plants of the new *Caladium* differ primarily from plants of the male parent, 'Miss Muffet', in the following characteristics:

1. Plants of the new *Caladium* are taller than plants of 'Miss Muffet'.
2. Leaves of plants of the new *Caladium* are broader than leaves of plants of 'Miss Muffet'.
3. Plants of the new *Caladium* and 'Miss Muffet' differ in leaf coloration as leaves of plants of 'Miss Muffet' have red-colored venation, lime green interveinal areas and red-colored spots.

Plants of the new *Caladium* can be compared to plants of *Caladium* 'Raspberry Moon', disclosed in U.S. Plant Pat. No. 20,069. In side-by-side comparisons conducted in Avon Park, Fla., plants of the new *Caladium* differed primarily from plants of 'Raspberry Moon' in the following characteristics:

1. Plants of the new *Caladium* were taller and more vigorous than plants of 'Raspberry Moon'.
2. Leaves of plants of the new *Caladium* were more rounded than and not as undulate as leaves of plants of 'Raspberry Moon'.

3. Plants of the new *Caladium* and 'Raspberry Moon' differed in leaf coloration as leaves of plants of 'Raspberry Moon' were light green in color with random dark green and red-colored spots and splotches.

Plants of the new *Caladium* can also be compared to plants of *Caladium* 'Aaron', not patented. In side-by-side comparisons conducted in Avon Park, Fla., plants of the new *Caladium* differed primarily from plants of 'Aaron' in the following characteristics:

1. Plants of the new *Caladium* were taller than plants of 'Aaron'.
2. Plants of the new *Caladium* grew faster than plants of 'Aaron'.
3. Plants of the new *Caladium* and 'Aaron' differed in leaf coloration as leaves of plants of 'Aaron' have white-colored venation and radiating interveinal areas surrounded with green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Sweet Carolina' grown in a 15-cm container in a shadehouse.

The photograph at the top of the second sheet is a top perspective view of typical plants of 'Sweet Carolina' grown in an outdoor nursery.

The photograph at the bottom of the second sheet is a close-up view of typical freshly-harvested tubers and roots of 'Sweet Carolina'.

The photograph on the third sheet is a close-up view of typical inflorescences of 'Sweet Carolina'.

The photograph at the top of the fourth sheet is a comparison view of typical potted plants of the female parent, 'Grey Ghost' (left) and 'Sweet Carolina' (right).

The photograph at the bottom of the fourth sheet is a side perspective view of a typical potted plant of the male parent, 'Miss Muffet'.

The photograph at the top of the fifth sheet is a side perspective view of a typical potted plant of 'Raspberry Moon'.

The photograph at the bottom of the fifth sheet is a side perspective view of a typical potted plant of 'Aaron'.

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the summer in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were seven weeks old when the photographs and the detailed description were taken. Plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Sweet Carolina'.

Parentage:

*Female, or seed, parent.*—*Caladium×hortulanum* 'Grey Ghost', not patented.

*Male, or pollen, parent.*—*Caladium×hortulanum* 'Miss Muffet', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments relatively large and elliptic in shape. Height: About 3.3 cm. Diameter: About 5.5 cm. Texture: Thick and starchy; somewhat brittle. Color: Epidermis, freshly harvested, close to 199A; epidermis, dried tuber, close to 200C to 200D; interior, close to 5C; axillary buds, close to 155D. Root description: Thick, fleshy contractile roots; color, close to 155D. Rooting habit: Few lateral branches; moderately dense.

Plant description:

*Plant type.*—Herbaceous perennial; suitable as a potted plant in containers 15-cm to 25-cm and suitable as a landscape plant in shaded and full sun areas.

*Plant and growth habit.*—Upright and mounding plant habit; tall plant size; inverted triangle; vigorous and dense growth habit; rapid growth rate; petioles and leaves arise from one or more growing points on tubers; petioles mostly upright and slightly leaning outwardly with development.

*Plant height, from soil level to top of foliar plane, shadehouse-grown potted plants.*—About 30 cm.

*Plant height, from soil level to top of inflorescences, shadehouse-grown potted plants.*—About 37.5 cm.

*Plant diameter or spread, shadehouse-grown potted plants.*—About 38 cm.

*Number of clumps per plant, shadehouse-grown potted plants.*—About six from de-eyed tubers.

*Cataphylls, shadehouse-grown potted plants.*—Length: About 11 cm. Width: About 2 cm. Shape: Lanceolate to elliptic. Apex: Acuminate. Base: Sheathing the stem. Color, outer surface: Close to 147C and N170D streaked, stippled and tessellated with close to N186A; with development, color becoming closer to 200A tinged with close to 187C. Color, inner surface: Lighter than 170D streaked with close to N186A.

Foliage description:

*Length, shadehouse-grown potted plants.*—About 20 cm.

*Width, shadehouse-grown potted plants.*—About 15.5 cm.

*Shape.*—Ovate.

*Apex.*—Acuminate to cuspidate.

*Base.*—Sagittate, peltate.

*Margin*.—Entire; mostly flat with some broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Basal notch: Close to 60A to 60B. Petiole attachment and adjacent veins: Close to 59A to 59B. Midrib: Close to 185A to 185B. Primary and secondary venation: Close to 185A to 185B. Interveinal areas: Random sectors, darker than 137A and close to 145C to 145B; random spots, close to N57D. Margins: Close to 185A to 185B. Developing leaves, lower surface: Basal notch: Close to 187B to 187C. Petiole attachment and adjacent veins: Close to 147C tinged with close to 65D. Midrib: Close to 147C tinged with close to 65D. Primary and secondary venation: Close to 147C tinged with close to 65D. Interveinal areas: Random sectors, close to 147A, 146A, 145C to 145D and 193C; random spots, close to 186A to 186B. Margins: Close to 145C to 145D tinged with close to 185A to 185B. Fully expanded leaves, upper surface: Basal notch: Close to 59A. Petiole attachment and adjacent veins: Close to 59A. Midrib: Close to 185A. Primary and secondary venation: Close to 185A. Interveinal areas: Random sectors, darker than 137A and close to 145B to 145C; flushing, close to 182A; random spots, close to 59C to 59D. Margins: Close to 187B to 187C. Fully expanded leaves, lower surface: Basal notch: Close to 187B to 187C. Petiole attachment and adjacent veins: Close to 147C tinged with close to 65D. Midrib: Close to 147C tinged with close to 65D. Primary and secondary venation: Close to 147C tinged with close to 65D. Interveinal areas: Random sectors, close to 148B to 148C, N189A, N189B and N138B; random spots, close to 186C. Margins: Close to 148C tinged on leaf edge with close to 187B to 187C.

*Petiole*.—Aspect: Mostly erect; flexible. Length, shadehouse-grown potted plants: About 22 cm. Diameter, distal, shadehouse-grown potted plants: About 4 mm. Diameter, proximal, shadehouse-grown potted plants: About 9 mm. Color, shadehouse-grown potted plants: Close to 147C to 177C to 177D striped, streaked, stippled and tessellated with close to N186C. Wing length, shadehouse-grown potted plants: About 4.6 cm. Wing diameter, shadehouse-grown potted plants: About 6 mm. Wing color, shadehouse-grown potted plants, outer surface: Close to 147C and N170D streaked, stippled and tessellated with close No N186A. Wing color, shadehouse-grown potted plants, inner surface: Colors visible from outer surface.

Inflorescence description: Inflorescences observed on twelve-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—None detected.

*Natural flowering season/longevity*.—Plants of the new *Caladium* typically flower during the spring or early summer in central Florida; flowers develop about twelve weeks after growth commences; inflorescences last about three days before fading; inflorescences persistent.

*Spathe*.—Length: About 13.5 cm; upper open length, about 9 cm and lower closed length, about 4.5 cm. Width, distal: About 4.2 cm. Width, proximal: About 3.9 cm. Width, at constriction: About 1.3 cm. Shape: Ovate to elliptic. Apex: Acuminate. Base: Tapering to the peduncle. Margin: Entire. Texture, upper and lower surfaces: Smooth, glabrous. Color, front surface, when opening: Upper two-thirds: Close to 155C and 145C to 145D. Lower one-third: Close to 148B to 148C darkly flushed with close to N77A. Color, front surface, fully opened: Upper two-thirds: Close to 155D; with development, color becoming closer to 27D and 173C. Lower one-third: Close to 148B darkly flushed with close to N77A; with development, color becoming closer to 147B. Color, rear surface, when opening: Upper two-thirds: Close to 158C to 158D tinged with close to 165B. Lower one-third: Close to 147B. Color, rear surface, fully opened: Upper two-thirds: Close to 158D tinged with close to 70D. Lower one-third: Close to 147B.

*Spadix*.—Length: About 9.8 cm. Length, male flower zone: About 6.2 cm. Length, sterile flower zone: About 1.4 cm. Length, female flower zone: About 2.2 cm. Diameter, male flower zone: About 1.1 cm. Diameter, sterile flower zone: About 6 mm. Diameter, female flower zone: About 1.1 cm. Shape: Columnar. Apex: Obtuse. Base: Obtuse. Aspect: Upright. Color, immature, male zone: Close to 155D. Color, immature, sterile zone: Close to 155D. Color, immature, female zone: Close to 158D. Color, mature, male zone: Close to 155D. Color, mature, sterile zone: Close to 155D. Color, mature, female zone: Close to 16D. Male flowers: Quantity per spadix: About 150. Shape: Obovate. Height: About 4 mm. Diameter: About 4 mm. Pollen amount: Abundant. Pollen color: Close to 12D. Female flowers: Quantity per spadix: About 90. Shape: Ovate to elliptic. Height: About 3 mm. Diameter: About 3 mm. Stigma color: Close to 16C to 16D. Ovary color: Close to 16D.

*Scape*.—Length: About 32 cm. Diameter: About 7.5 mm. Strength: Sturdy; flexible. Aspect: Erect. Texture: Smooth, glabrous; glaucous. Color: Close to 147C and 177C to 177D striped and streaked with close to N186C.

*Seeds and fruits*.—Seed and fruit development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Sweet Carolina' as illustrated and described.

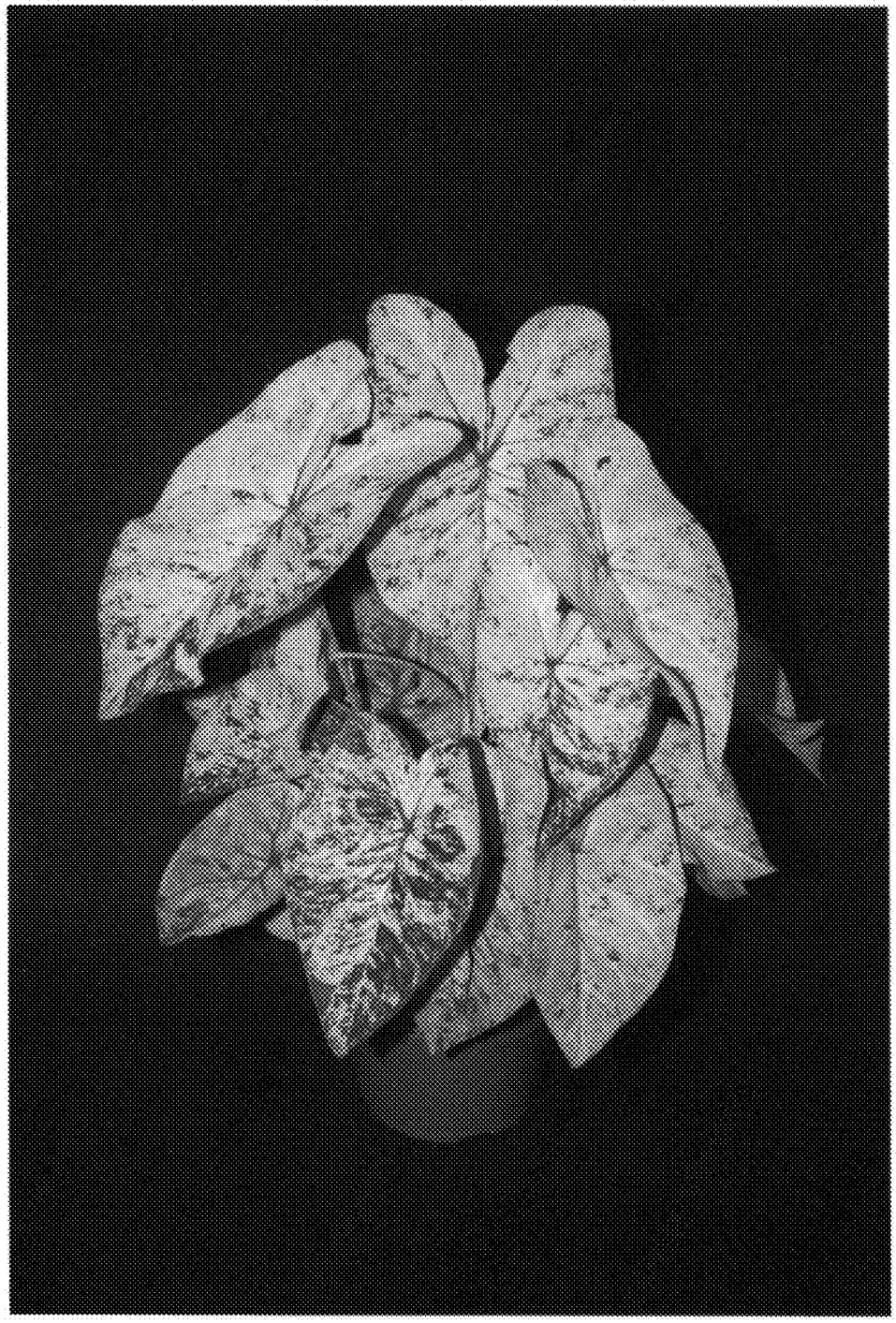

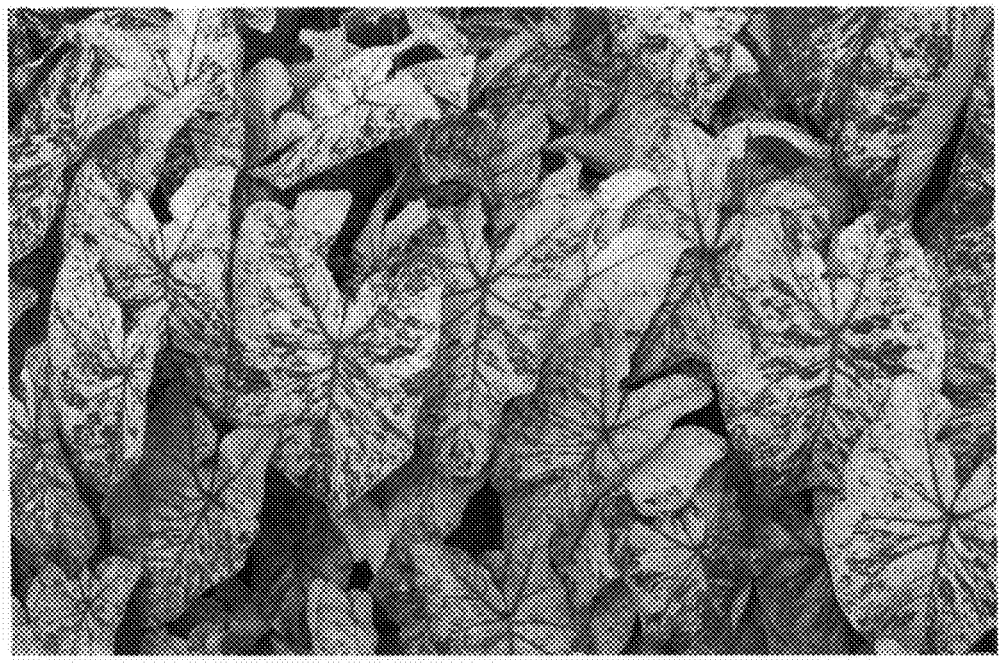
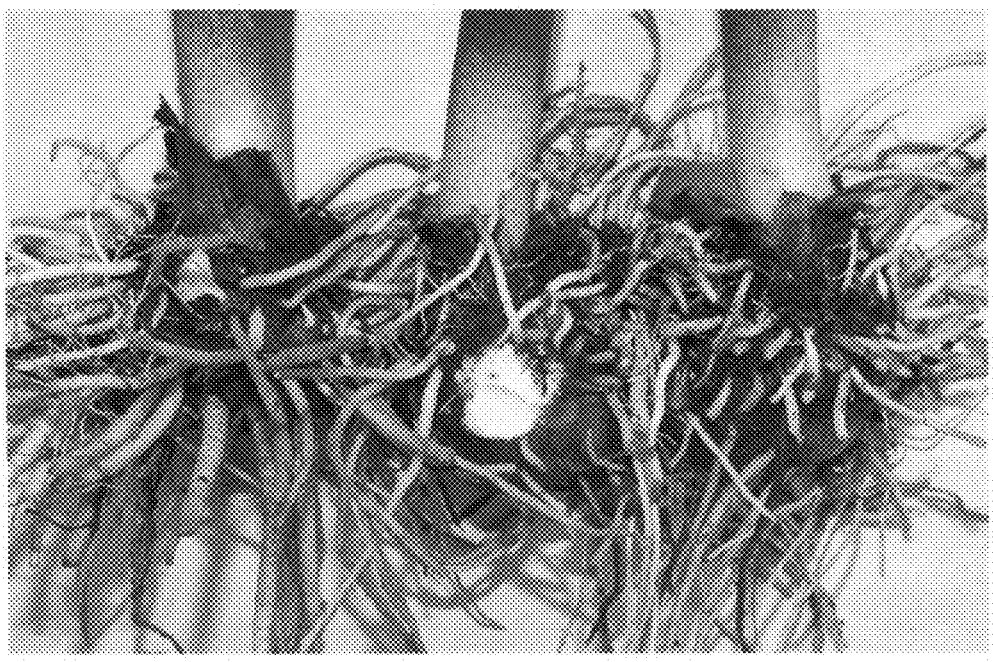

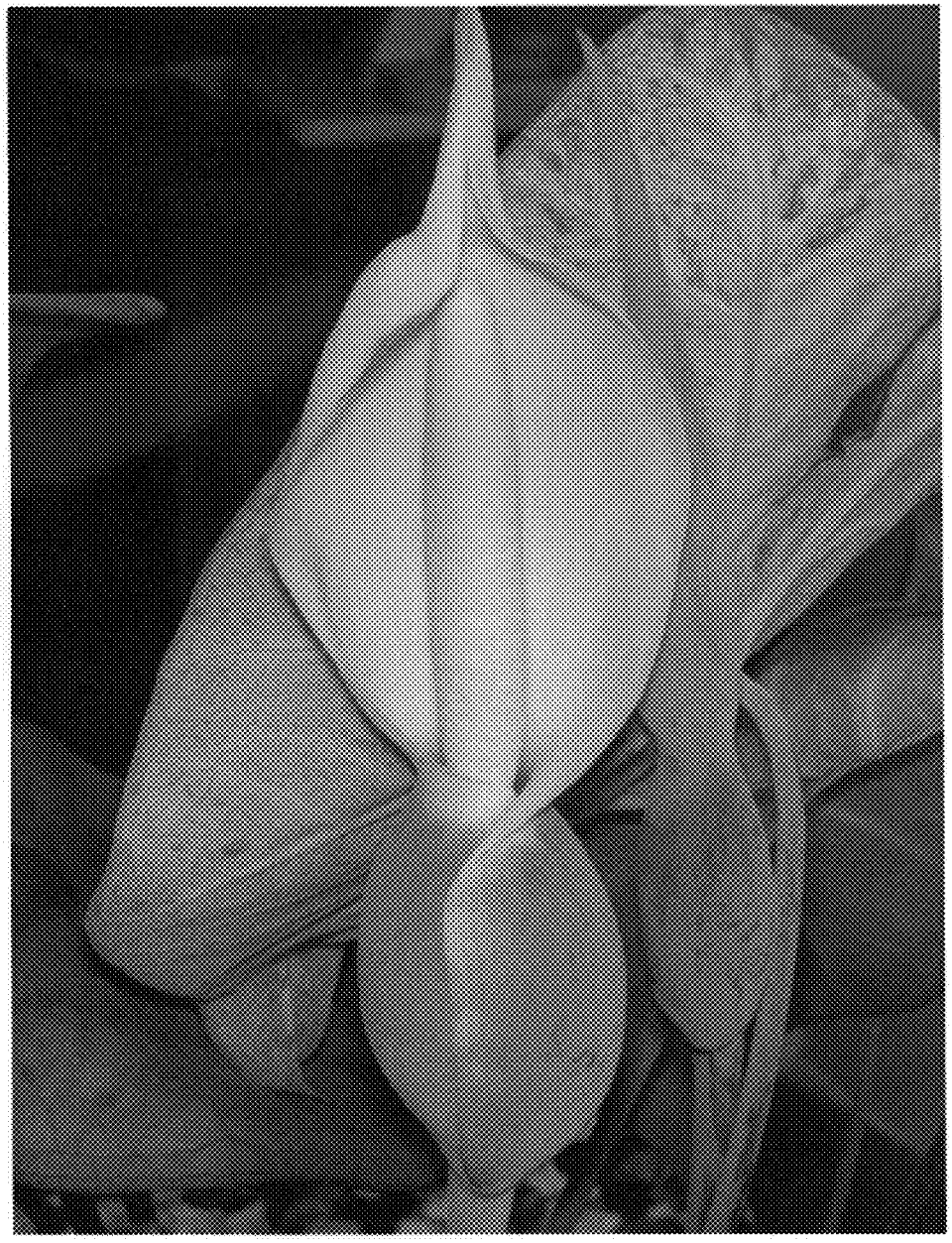

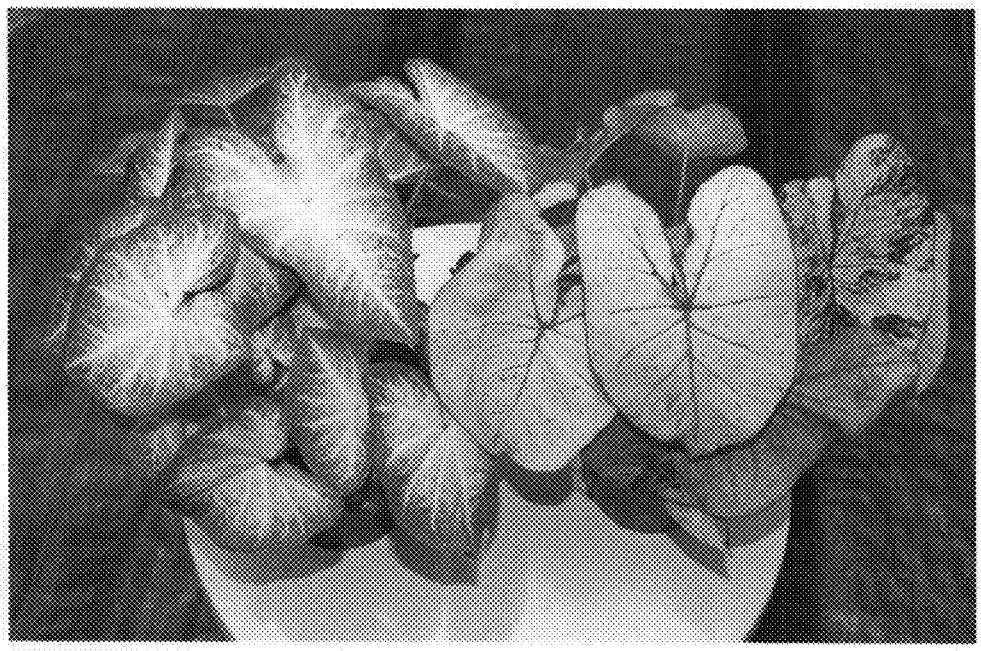
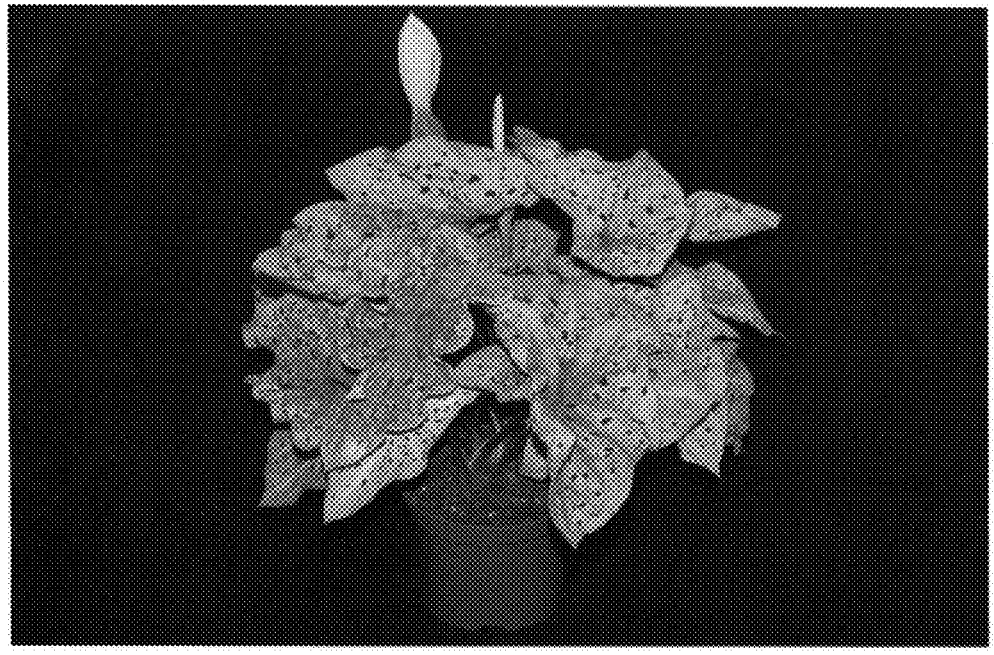

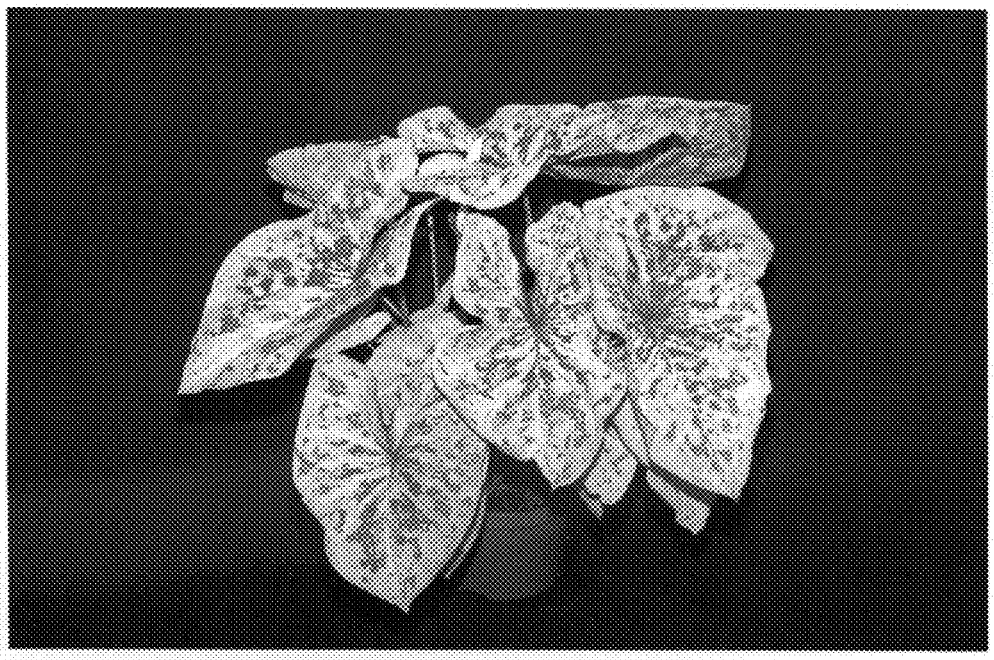
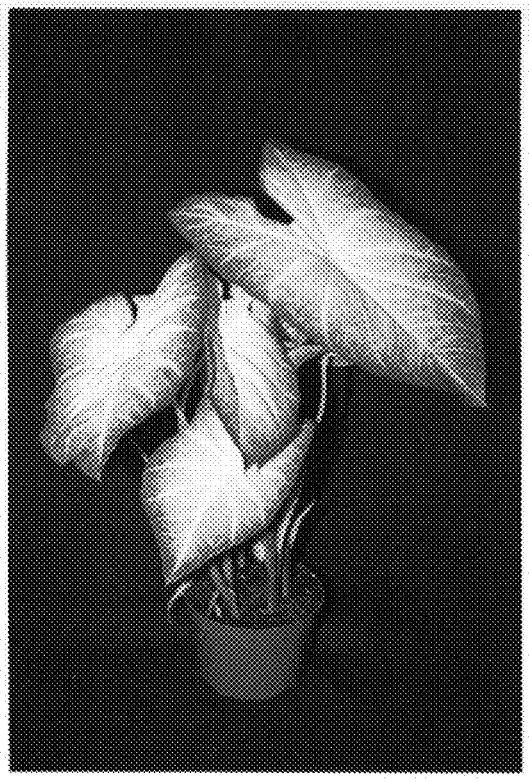

* * * * *